Dec. 18, 1956 R. CASADABAN Plant Pat. 1,539
CAMELLIA PLANT
Filed Jan. 30, 1956
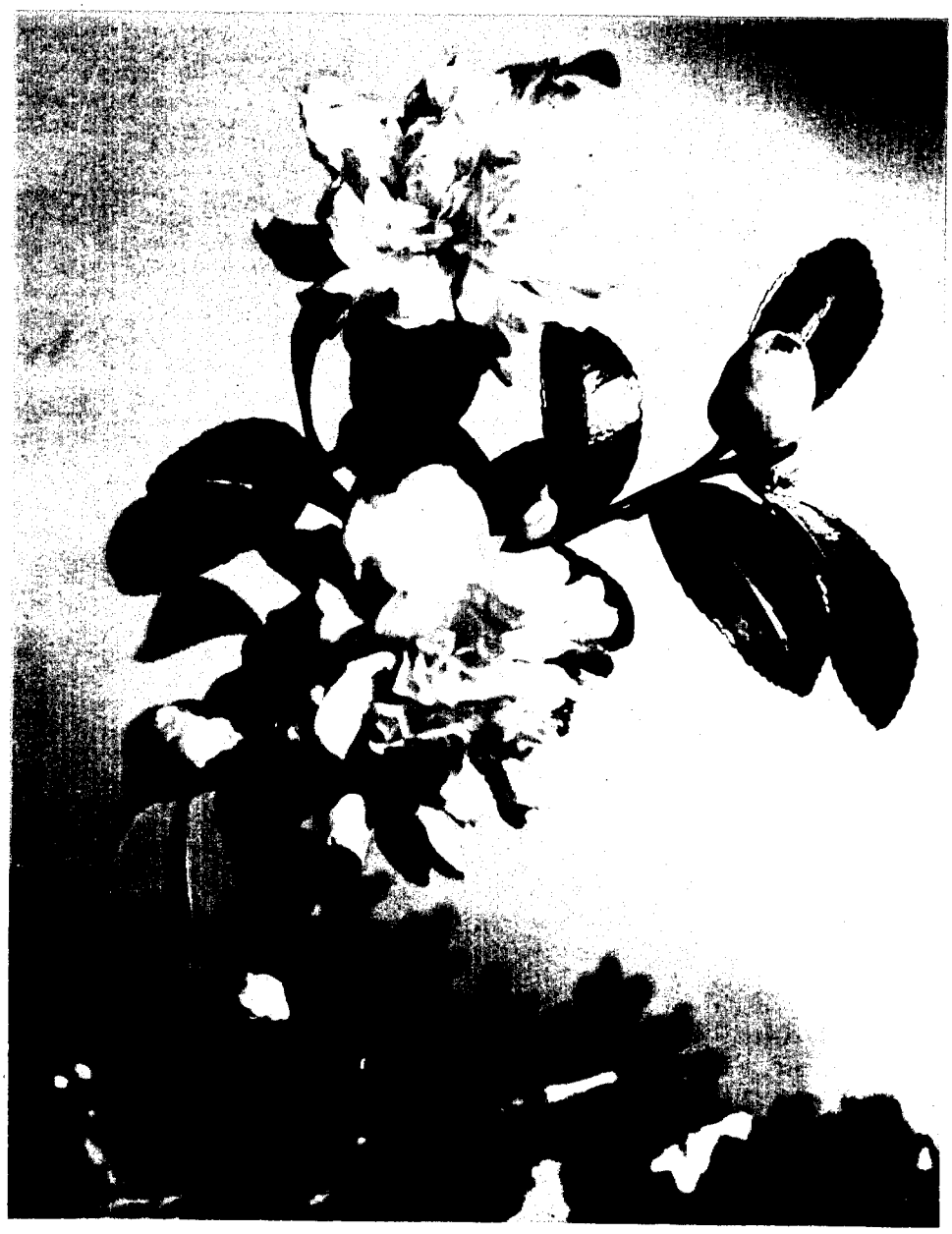
Inventor.
Rene Casadaban
By: Robb & Robb
Attorneys.

United States Patent Office

Plant Pat. 1,539
Patented Dec. 18, 1956

1,539

CAMELLIA PLANT

Rene Casadaban, Abita Springs, La.

Application January 30, 1956, Serial No. 562,353

1 Claim. (Cl. 47—60)

The present invention relates to a new and distinct variety of camellia plant of the Sasanqua class, which was originated by me by crossing the variety "Hino-de-gumo" (unpatented) with the variety "Showa-no-Sakae" (unpatented).

As the result of this breeding, I have produced a new camellia variety of the Sasanqua class which is particularly characterized as to novelty and distinguished from all other camellia varieties, including the parent varieties, by its strong and improved habits of growth, its free-blooming habit, and its distinctive double, red-colored flowers which are similar in general color tonality to the flowers of the variety "Shishi-gashira" (unpatented).

Asexual reproduction of my new variety by both cuttings and grafting, as performed by me at Abita Springs, Louisiana, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert F. Wilson's Horticultural Color Chart, except where general color terms of ordinary dictionary significance are obvious:

Parentage: Seedling.
- *Seed parent.*—"Hino-de-gumo."
- *Pollen parent.*—"Showa-no-Sakae."

Propagation: Holds its distinguishing characteristics through succeeding propagations by cuttings and grafting.

Blooming habit: Early.

Bud:
- *Size.*—Medium.
- *Form.*—Pointed.
- *Sepals.*—Smooth edge.
- *Calyx.*—Shape—apple; size—small.

Bloom:
- *Size (when fully open).*—Large; from 2½ inches to 3 inches in diameter.
- *Borne.*—Usually 2 per stem; on strong, short stems.
- *Form.*—When first petal opens—cup-shaped; when fully opened—peony formed.
- *Petalage.*—Double; irregular.
- *Color.*—Rose Bengal, Plate 25/1 (Wilson).

Petals: From thick to thin; with inside shiny and outside from shiny to velvety.
- *Shape.*—Lanceolate.
- *Arrangement.*—Irregular.

Genital organs:
- Stamens.—Medium length. Color—Chrome Yellow, Plate 605/1 (Wilson). Arrangement—sparse.
- Stamens, filaments.—Short. Color—Lemon Yellow.
- Pollen.—Color—Gold.
- Styles.—Bunched; even length; short. Color—Cream.
- Ovaries.—All enclosed in calyx.

Fruit: Sterile to own pollen.
- *Form.*—Round.
- *Aspect.*—Hairy.
- *Color at maturity.*—Gray-Brown.
- *Sepals.*—Pear-shaped.

Plant:
- *Form.*—Bush.
- *Growth.*—Very vigorous; upright; branching.

Foliage:
- *Size.*—Medium.
- *Quantity.*—Abundant.
- *Color.*—New foliage—Fern Green, Plate 862/1 (Wilson). Old foliage—Spinach Green, Plate 960/1 (Wilson).
- *Shape.*—Oval pointed.
- *Texture.*—Upper side—glossy; smooth. Under side—smooth.
- *Ribs and veins.*—Ordinary.
- *Edge.*—Serrated.

Disease and insect resistance: Generally similar to other Sasanqua camellias, as determined by comparison with other varieties grown under comparable cultural conditions at Abita Springs, Louisiana.

Wood:
- *New wood.*—Color—Reddish Brown.
- *Old wood.*—Color—Brown.

I claim:

A new and distinct variety of camellia plant of the Sasanqua class, substantially as herein shown and described, characterized particularly as to novelty by its strong and improved growing habits, its free-blooming habit, and by its double flowers of Red general color tonality comparable to the color of the flowers of the variety "Shishi-gashira" (unpatented).

No references cited.